US005382526A

United States Patent [19]

Gajewski et al.

[11] Patent Number: 5,382,526

[45] Date of Patent: Jan. 17, 1995

[54] BLOOD STORAGE CONTAINER AND MATERIAL

[75] Inventors: Henry M. Gajewski, Winnetka; Barry H. Vernick, McHenry; Paul E. Measells, Libertyville; Jan W. Garber, McHenry, all of Ill.

[73] Assignee: Baxter International Inc., Deerfield, Ill.

[21] Appl. No.: 326,449

[22] Filed: Mar. 17, 1989

Related U.S. Application Data

[63] Continuation of Ser. No. 173,014, Mar. 21, 1988, abandoned, which is a continuation of Ser. No. 52,220, May 19, 1987, abandoned, which is a continuation of Ser. No. 906,651, Sep. 11, 1986, abandoned, which is a continuation of Ser. No. 786,183, Oct. 10, 1985, abandoned, which is a continuation of Ser. No. 690,692, Nov. 11, 1985, abandoned, which is a continuation of Ser. No. 471,745, Mar. 9, 1983, Pat. No. 4,507,387, which is a continuation of Ser. No. 202,515, Oct. 31, 1980, abandoned.

[51] Int. Cl.[6] .................... C12M 1/24

[52] U.S. Cl. .................... 435/296; 435/260; 524/140; 524/297; 524/298; 524/567

[58] Field of Search .................... 524/567, 140, 297, 298; 435/2, 243, 260

[56] References Cited

U.S. PATENT DOCUMENTS

| | | |
|---|---|---|
| 2,406,802 | 9/1946 | Carruthers . |
| 2,642,866 | 6/1953 | Smith . |
| 2,831,824 | 4/1958 | White . |
| 2,896,619 | 7/1959 | Bellamy, Jr. . |
| 3,043,792 | 7/1962 | Horwitz . |
| 3,645,955 | 2/1972 | Flynn . |
| 3,872,154 | 3/1975 | Hirzy . |
| 3,888,909 | 6/1975 | Hendrickreim . |
| 3,915,922 | 10/1975 | Suzuki et al. . |
| 3,940,802 | 3/1976 | Sako et al. . |
| 3,956,220 | 5/1976 | Reim et al. . |
| 4,007,218 | 2/1977 | Ghanayem et al. . |
| 4,247,440 | 1/1981 | Asai et al. . |
| 4,280,497 | 7/1981 | Warner et al. . |
| 4,286,597 | 9/1981 | Gajewski et al. . |
| 4,300,559 | 11/1981 | Gajewski et al. . |
| 4,301,800 | 11/1981 | Collins . |
| 4,326,025 | 4/1982 | Buckles et al. . |
| 4,375,509 | 3/1983 | Buckles et al. . |
| 4,451,259 | 5/1984 | Geissler et al. . |
| 4,507,387 | 3/1985 | Gajewski et al. . |
| 4,670,013 | 6/1987 | Barnes et al. .................... 604/403 |

FOREIGN PATENT DOCUMENTS

| | | |
|---|---|---|
| 0051414 | 5/1982 | European Pat. Off. . |
| 0114372 | 8/1984 | European Pat. Off. . |

OTHER PUBLICATIONS

Harold Sarvetnick, *Polyvinyl Chloride*, Reinhold Plastics Application Series, copyright 1969, pp. 70–87.
Chemical Abstracts, vol. 70, No. 7 (Feb. 19, 1973).

*Primary Examiner*—Christopher Henderson
*Assistant Examiner*—N. Sarofim
*Attorney, Agent, or Firm*—Bradford R. L. Price; Paul C. Flattery; Daniel D. Ryan

[57] ABSTRACT

A blood bag comprises a plastic polyvinyl chloride formulation in which the polyvinyl chloride formulation contains from 5 to 30 percent by weight of a first plasticizer material which is essentially nonextractable by blood plasma stored in the bag up to 35 days at about 4° C.; and from 10 to 25 percent by weight of a second plasticizer which is significantly extracted by blood plasma stored in the bag up to 35 days at about 4° C.

4 Claims, 1 Drawing Sheet

BLOOD STORAGE CONTAINER AND MATERIAL

Figure 1:
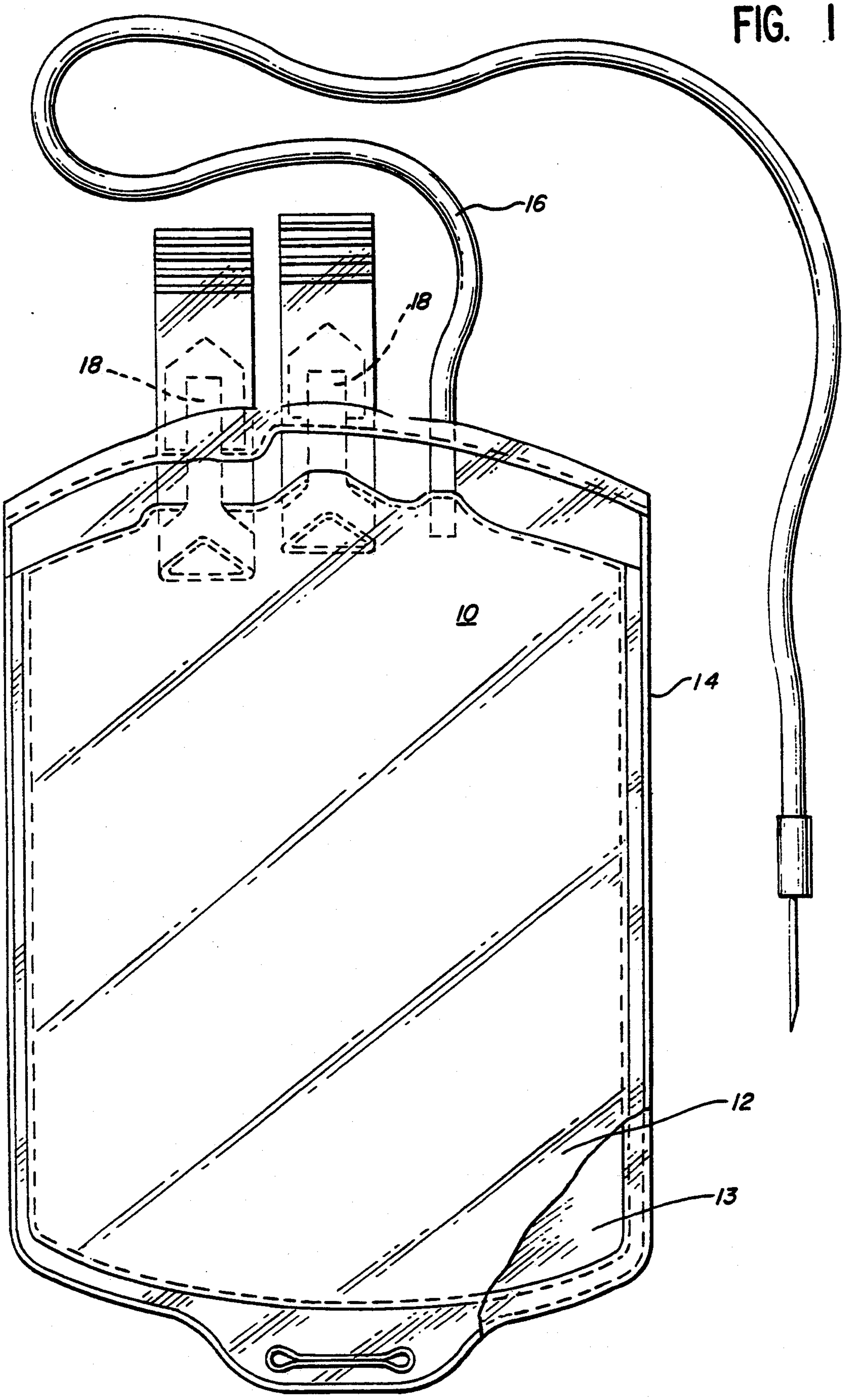

This is a continuation of application Ser. No. 07/173,014 filed Mar. 21, 1988 now abandoned, which is a continuation of application Ser. No. 52,220, filed May 18, 1987 now abandoned, which is a continuation of application Ser. No. 906,651 filed Sep. 11, 1986, now abandoned, which is a continuation of application Ser. No. 786,183, filed Oct. 19, 1985 now abandoned which is a continuation of application Ser. No. 690,692, filed Jan. 11, 1985, abandoned, which is a continuation of application Ser. No. 471,745, filed Mar. 9, 1983, U.S. Pat. No. 4,507,387 which is a continuation of application Ser. No. 202,515 filed on Oct. 31, 1980 (now abandoned).

BACKGROUND OF THE INVENTION

Single and multiple blood bags are commercially available for collecting blood and storing it, or, in the case of multiple bags, for processing the blood under sterile conditions to obtain various blood components that may be desired, for example, packed red cells, plasma, platelets, and cryoprecipitate.

The currently-available blood bags are made of a polyvinyl chloride formulation which includes, as a plasticizer, di-2-ethylhexylphthalate. Such a plasticizer is absolutely necessary for polyvinyl chloride formulations, since polyvinyl chloride itself is not a suitable, flexible plastic material for use in containers. Such blood bags have served extremely well in the storage and processing of blood and blood components, exhibiting a high survival rate with low plasma hemoglobin content after, for example, 21 days of storage at about 4° C.

However, such plasticized blood bags have been found to yield a detectable amount of the ester type plasticizer into the plasma of the blood as it is stored in the bag for a period of days. Typically, blood is stored up to 21 days, but in some special circumstances the storage time of viable blood cells has been extended up to 35 days at conventional storage temperatures. On a typical storage of 21 days, whole blood in a plasticized blood bag may pick up approximately 50 to 80 parts per million of di-2-ethylhexylphthalate per ml., using the commercially available blood bags mentioned above.

While no significant undesirable effects of the di-2-ethylhexylphthalate have been discovered, many physicians and others feel that it would be naturally desirable to keep the concentration of the ester plasticizer which leaches into the blood on storage to a minimum.

Other, chlorine-free plastic formulations have been tested as candidate blood bag materials as well, including flexible polyesters, polyolefins, and the like. As described in Geissler U.S. application Ser. No. 105,469, filed Dec. 19, 1979 and entitled "Blood Compatible Materials and Medical Devices Made Therefrom", many plastic materials tested without containing ester-type plasticizers have caused blood stored in containers made of such materials under the usual blood storage conditions to exhibit an undesirably high plasma hemoglobin content, indicating that the lysis rate of the red blood cells is high.

It has been determined that the presence of an ester-type plasticizer such as di-2-ethylhexylphthalate in a certain low concentration is effective to suppress the lysis of red blood cells during the long-term storage of blood. Hence, the presence of an ester-type plasticizer, which is an ingredient thought by many to be undesirable because of its leaching characteristics into the blood, turns out to be a valuable component for blood storage to suppress red cell hemolysis.

In accordance with this invention, a blood bag is provided, made of a novel formulation in which the desirable effects of the blood extractable ester plasticizer in suppressing hemolysis on storage may be exploited, while at the same time a minimum desired concentration of the extractable ester-type plasticizer necessary to accomplish this end is provided. At the same time, the polyvinyl chloride blood bag may have the desired properties of softness, strength and collapsibility, which generally requires more plasticizer than is normally provided by the minimal concentration of extractable plasticizer necessary to achieve the desired antihemolytic effect.

By this invention, for the first time polyvinyl chloride blood bags may be formulated to their optimum physical characteristics having a sufficient concentration of plasticizer for that purpose, while at the same time the concentration of plasma-extractable, hemolysis-suppressing plasticizer may be at a lesser optimum concentration to provide the desired amount of red cell hemolysis suppression, coupled with a reduced concentration of the extractable plasticizer in the plasma of the stored blood, so that exposure to the plasticizer materials by a patient may be minimized.

DESCRIPTION OF THE INVENTION

In this invention a blood bag is provided, made of a plasticized polyvinyl chloride formulation. By the improvement of this invention, the polyvinyl chloride formulation contains from 5 to 30 percent by weight of a first plasticizer material which is essentially nonextractable by blood plasma stored in the bag up to 35 days at about 4° C. Also, the plasticizer for the polyvinyl chloride formulation contains from 10 to 25 percent by weight of a second plasticizer capable of suppressing red cell hemolysis on blood storage and physiologically compatible with blood, with preferably a total 25 to 40 percent of the first and second plasticizers being present. The second plasticizer is significantly extracted by blood plasma stored in the bag up to 35 days at 4° C.

The term "significantly extracted" is intended to mean, for purposes of this application, that in such a 35 day storage period the concentration of plasticizer in the blood rises to at least 10 parts per million. A plasticizer material which is "essentially nonextractable" by blood plasma stored in a bag up to 35 days at 4° C. contains a concentration of such a plasticizer of no more than 2 parts per million at the end of the storage period. In both of the above test cases, the tests are performed with a polyvinyl chloride formulation containing the plasticizer at the concentration that it is intended to be used.

Preferably, the first plasticizer is a fatty ester containing at least three ester linkages comprising fatty hydrocarbon groups of 4 to 12 carbon atoms each on a hydrocarbon chain. Examples of such materials include tri-n-hexyltrimellitate, trioctyltrimellitate, and triisonoyltrimellitate. Preferably tri-2-ethylhexyltrimellitate may be used as the nonextractable plasticizer in the blood bag formulation of this invention. Preferably, the first plasticizer may be present in the formulation in a concentration of 10 to 20 percent by weight.

The second, extractable plasticizer is preferably a fatty ester containing two ester linkages comprising fatty hydrocarbon groups of 4 to 12 carbon atoms each on a hydrocarbon chain. Specifically, dialkylphthalates, in which each alkyl radical contains from 7 to 10 carbon atoms and preferably having branched chains are one preferred category of material for the second plasticizer utilized herein. Such materials are generally capable of causing a reduction in the hemolysis of the stored blood, when compared with blood under similar storage conditions in a container free of the plasma-extractable materials. Preferably from 12 to 20 percent by weight of the second plasticizer is present.

The reference above to the extractability or non-extractability of the plasticizers by blood plasma is not intended to exclude the presence of whole blood. The containers of this invention are commonly used for the storage of whole blood. However, such whole blood of course contains plasma, and it is believed, without wishing to be limited to any theory of operation, that the prime route of plasticizer extraction is from the bag walls to the plasma in the blood. Also, blood plasma freed of its cells will exhibit similar extracting behavior of the second plasticizer used in this invention, although the prime benefit of the second plasticizer of this invention is found in its suppression of the hemolysis of red cells on long-term storage.

The fatty hydrocarbon groups in the ester linkages (e.g., $$R{-}O\overset{\displaystyle O}{\overset{\|}{C}}{-}\ )$$

are preferably alkyl radicals of 7 to 10 carbon atoms. In the second extractable plasticizer, the ester linkages are preferred to be attached to adjacent carbon atoms in the chain, although good results can be obtained from more widly based ester groups if the hydrocarbon chain is highly mobile, for example, a saturated linear hydrocarbon chain as in di-2-ethylhexyladipate.

Examples of the fatty hydrocarbon groups of the ester linkages are the preferred alkyl radicals such as octyl, heptyl, nonyl, decyl, or 2-ethylhexyl. Preferably, the fatty hydrocarbon groups are branched Other radicals such as hexyl and dodecyl may also be used. Also, similar alkenyl radicals such as octenyl, nonenyl, or decenyl, containing one or more unsaturated linkages, may be used.

Examples of the preferred ester materials for the second plasticizer are the dioctylphthalates and dioctyladipates, diisononylphthalate, and diisodecylphthalate. Other antihemolytic agents which may be used include di-2-ethylhexylmaleate, dibutylphthalate, dihexylphthalate, didodecylphthalate, di-2-ethylhexylazalate, di-2-ethylhexylisophthalate, and di-2-ethylhexylmaleate, all of which exhibit antihemolytic properties when in dispersed contact with blood.

Alternatively, the second plasticizer may be an ester of a phosphoric acid containing at least two ester linkages comprising fatty hydrocarbon groups of 4 to 12 carbon atoms each. For example, trioctylphosphate (and specifically tri-2-ethylhexylphosphate) provides both plasticizing characteristics for the polyvinyl chloride formulation and the antihemolytic effect utilized in this invention. Other examples of such phosphate esters include trihexylphosphate, triheptylphosphate and diisodecylphosphate.

Also, if desired, mixed esters may be utilized in each of the above cases where different fatty hydrocarbon groups participate in the ester linkage; for example, octyl-decylphthalate or decyldihexylphosphate.

If desired, only portions of the bag materials which are in contact with the blood contained therein may contain the second plasticizer material of this invention. Alternatively, a plastic insert member such as a sheet of plastic, plastic beads, or the like made of the vinyl formulation of this invention may be positioned within a blood bag and may contain the second antihemolytic material in combination with the first material, while the actual bag walls may be relatively free of such plasticizer materials and may constitute a different plastic entity, for example a polyester or a polyolefin. Both of these circumstances are generally equivalent to the preferred use of a blood bag made out of the plasticized polyvinyl chloride formulation in accordance with this invention throughout essentially the entire material of the bag.

It may be desirable to incorporate the blood bag of this invention into a multiple bag system containing a plurality of blood bags connected by tubing. The additional blood bags may be of different construction from the bag of this invention, for example, as taught in Smith U.S. application Ser. No. 955,059, filed Oct. 26, 1978.

Referring to the drawings, FIGURE 1 is a plan view of a blood bag made in accordance with this invention, with a portion broken away.

Blood bag 10 may be made of conventional construction, including a pair of plastic sheets 12, 13 sealed at periphery 14, and containing a blood collection tube 16 (which may be made of the composition of this invention), having the usual donor needle and a pair of sealed access ports 18.

In accordance with this invention, bag 10 is made from a transparent, flexible, sterilizable plasticized polyvinyl chloride formulation which contains preferably about 32 percent by weight of plasticizer for the polyvinyl chloride. The plasticizer, in turn, typically may constitute about 17 percent by weight of tri-2-ethylhexyltrimellitate, in intimate mixture with 15 percent by weight of di-2-ethylhexylphthalate. Accordingly, the plasticized polyvinyl chloride is both flexible and strong for suitable use as a blood bag.

When the blood bag 10 is filled in conventional manner through donor tube 16 with blood, it may then be stored in conventional manner. Bag 10 may contain an appropriate blood preservative such as ACD or CPD solution as is conventional for storage of the blood.

During storage, amounts of the di-2-ethylhexylphthalate plasticizer pass from the plastic to the blood plasma and into interaction with the red cells, effectively suppressing the amount of hemoglobin which is generated over the storage period of days, compared with blood stored in a bag which is free of the extractable plasticizer. At the same time, the concentration of extractable plasticizer leaching into the blood is substantially less than would be found in the situation of a commercially available blood bag plasticized exclusively with di-2-ethylhexylphthalate, so that the blood contains only a minimum concentration of di-2-ethylhexylphthalate necessary to keep the hemolysis level of blood below a desired amount. Nevertheless, the physical properties of the blood bag itself remain optimum because of the presence of the added first plasticizer which is essentially nonextractable by blood plasma present in the whole blood.

For example, polyvinyl chloride blood bags were made of a plasticized formulation as described below, and whole blood was collected and stored at 4° C. in the blood bags for 28 days under conventional conditions. The blood bags contained the conventional CPD blood preservative.

The blood bags of formulation 1 were commercially available, polyvinyl chloride blood bags containing di-2-ethylhexylphthalate plasticizer (manufactured by Fenwal Laboratories, a division of Travenol Laboratories, Inc.).

The blood bags of formulation 2 were of a plasticized polyvinyl chloride formulation containing 15 percent by weight of di-2-ethylhexylphthalate and 17 percent by weight of tri-2-ethylhexyltrimellitate, and otherwise similar to the blood bags of formulation 1.

The blood bags of formulation 3 were of a polyvinyl chloride formulation containing exclusively tri-2-ethylhexyltrimellitate as the plasticizer in a concentration of about 32 percent by weight, and otherwise similar to the blood bags of formulation 1.

The table below illustrates the average amount of plasma hemoglobin produced by each of these blood bags under conventional storage conditions.

| Days of Storage | Plasma Hemoglobin Formed (milligrams per deciliter) | | |
|---|---|---|---|
| | Formulation 1 | Formulation 2 | Formulation 3 |
| 14 | 18 | 23 | 27 |
| 21 | 27 | 33 | 37 |
| 28 | 35 | 43 | 47 |
| 35 (extrapolated) | 43 | 54 | 57 |

The amount of di-2-ethylhexylphthalate present in the blood was as follows:

After 14 days, the bag of formulation 1 contained 48, and the bags of formulation 2 contained 22 (on the average) micrograms of di-2-ethylhexylphthalate per ml.

After 28 days of storage, the blood of the bags of formulation 1 contained 96 and the blood of the bags of formulation 2 contained 43 (on the average) micrograms per ml. of di-2-ethylhexylphthalate.

The blood in the bags of formulation 3 were tested for their extracted concentration of triethylhexyltrimellitate after 35 days of storage. The concentration was found to be less than 2 parts per million. Frequently, the concentration is substantially less than 1 part per million, although accuracy of measurement becomes difficult at these lower concentrations.

Accordingly, it can be seen that a blood bag of the formulation of this invention (formulation 2) can be utilized to store blood with a significant reduction in the leaching of plasticizer into the blood plasma. At the same time, a reduction of the plasma hemoglobin generated in the blood upon storage can be achieved, when compared with a blood bag which contains only an essentially nonextractable plasticizer.

The above has been offered for illustrative purposes only, and is not intended to limit the scope of the invention of this application, which is as defined in the claims below.

That which is claimed is:

1. A container for storage of blood or blood components comprising polyvinyl-chloride plasticized with a mixture of plasticizers, said mixture comprising from about 5 percent to about 30 percent by weight of a first plasticizer material which is essentially nonextractable by blood plasma during the storage period, and from about 10 percent to about 25 percent by weight of trioctylphosphate plasticizer capable of suppressing red cell hemolysis during the storage period and being physiologically compatible with blood, said trioctylphosphate plasticizer being sufficiently extracted by blood plasma stored in said bag such that, in a 35 day storage period, the concentration of said trioctylphosphate plasticizer in blood plasma rises to at least 10 parts per million.

2. A container according to claim 1 wherein the total amount of said plasticizer mixture is from about 25 to about 40 percent by weight.

3. A container according to claim 1 wherein said first plasticizer material is a trimellitate ester containing three fatty hydrocarbon groups of 4 to 12 carbon atoms each.

4. A container according to claim 1 wherein said first plasticizer material comprises a fatty ester containing at least three ester linkages comprising fatty hydrocarbon groups of at least four carbon atoms each on a hydrocarbon chain.

* * * * *